United States Patent [19]

Fridolph et al.

[11] 3,952,749
[45] Apr. 27, 1976

[54] BOX LOCK SURGICAL INSTRUMENT

[75] Inventors: John Fridolph, Berlin, N.J.; Robert Wilson, Dresher; Rodney Kulp, Harleysville, both of Pa.

[73] Assignee: Pilling Co., Fort Washington, Pa.

[22] Filed: May 7, 1975

[21] Appl. No.: 575,353

Related U.S. Application Data

[62] Division of Ser. No. 469,967, May 15, 1974, Pat. No. 3,911,766.

[52] U.S. Cl. ................................ 128/321; 30/254; 76/104 A; 81/416
[51] Int. Cl.² ................ A61B 17/28; B21K 11/06; B25B 7/06
[58] Field of Search ............... 30/254; 76/104 A; 81/416; 128/321, 325, 346

[56] References Cited
UNITED STATES PATENTS

| | | | |
|---|---|---|---|
| 1,852,542 | 4/1932 | Sovatkin | 128/321 UX |
| 2,939,214 | 6/1960 | Andersson et al. | 81/416 X |

*Primary Examiner*—Channing L. Pace
*Attorney, Agent, or Firm*—Smith, Harding, Earley & Follmer

[57] ABSTRACT

By electrically fusing a pin between the outer elements of a box hinge, and thereafter performing the hardening step, stresses which tend to cause instrument failures after a period of use are eliminated. Even if the pin fractures during use, the fact that it is fused to the outer elements of the box hinge prevents broken-off parts of the pin from falling out of the instrument.

4 Claims, 11 Drawing Figures

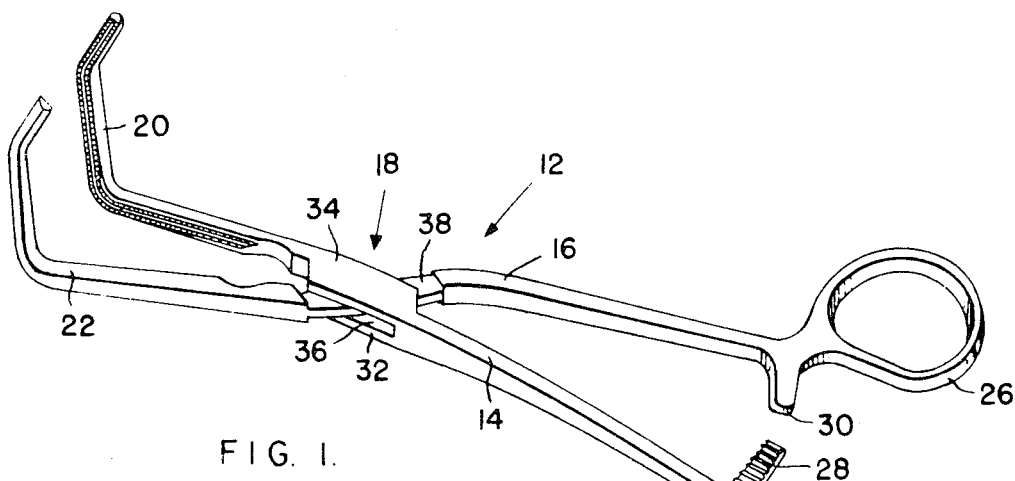
FIG. 1.
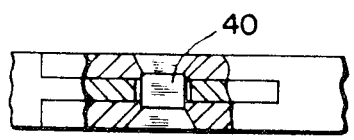
FIG. 2.
FIG. 3.
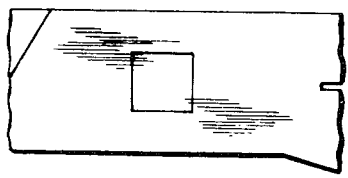
FIG. 4.
FIG. 5.
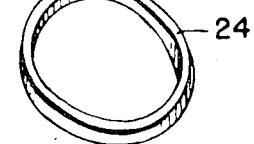
FIG. 6.
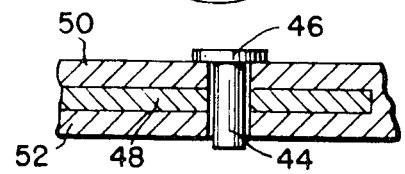
FIG. 7.
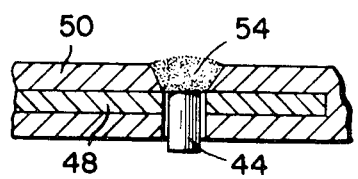
FIG. 8.
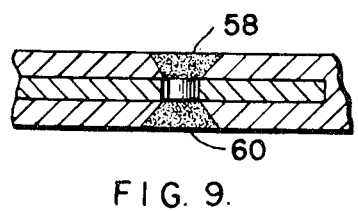
FIG. 9.

BOX LOCK SURGICAL INSTRUMENT

CROSS-REFERENCE TO RELATED APPLICATION

This is a division of our application Ser. No. 469,967 filed May 15, 1974, now U.S. Pat. No. 3,911,766 issued Oct. 14, 1975.

BACKGROUND OF THE INVENTION

This invention relates to surgical instruments, and particularly to the so-called "box lock" instruments. Instruments such as forceps, hemostats, and clamps are often provided with box lock joints particularly where a high degree of reliability and the very accurate meeting of grasping members is required.

The box lock joint is a special hinge used in instruments of the type comprising first and second members each having, at one end, operative means such as a clamping or gripping jaw adapted to cooperate with the operative means of the other member, and each having at its opposite end manipulable means, typically a ring handle, for controlling the movement of the operative means on the same member. The first member has a bifurcated portion at an intermediate location whereby its operative means and its manipulable means are connected to two separate elements having a slot between them. The second member extends through the slot with its operative means and its manipulable means on opposite sides of the bifurcated portion of the first member. A pin, extending across the slot and through a hole in the portion of the second member within the slot, completes the hinge and allows the operative means to be controlled by the manipulable means for clamping, depending on the nature of the particular instrument. The box lock joint is generally preferred because of its strength, the low degree of play which it allows, and its resistance to working loose. These characteristics are of particular importance in special instruments wherein the accurate cooperation of opposed operative means is required. This is the case, for example, with surgical clamping means having jaws specially designed to clamp tubular vessels of the body with the avoidance of damage thereto such as those described in U.S. Pat. No. 3,608,554, issued Sept. 28, 1971.

Heretofore, forceps and other surgical instruments having box lock joints were typically made by producing aligned holes in the two members to be joined, inserting a temporary pin, performing the necessary bending operations as well as grinding and polishing operations, removing the temporary pin, punching the holes in the bifurcated portion of the first member to a square or star configuration, hardening the first and second members, inserting a second pin, swaging or peening the pin, and finally finishing the instrument. Swaging of the pin following hardening results in the setting up of stresses in the instrument which remain unrelieved when the instrument goes into use. When the instrument is subjected to the influences of superheated steam (autoclaving), repeated mechanical loads under surgical conditions, and corrosion caused by the various elements in the surgical environment, these stresses eventually, if not in a very short time, manifest themselves as cracks in and around the box lock joint. Instrument breakage often occurs at the location of these cracks, and can constitute a serious safety hazard if it takes place during surgery.

In some cases, the hinge pin is inserted and swaged prior to hardening. However, peening is sometimes required to tighten the pin when shrinkage occurs in the hardening process. This peening results in stresses similar to those which occur when the pin is swaged following hardening. The danger of breakage therefore exists in instruments made by this alternative method.

The hinge pin itself is also susceptible to breakage. Although it is not a common occurrence, if a hinge pin in a conventional instrument breaks, it is possible for a part of the pin to fall out of the instrument while in use. In surgery, such an occurrence also represents a serious hazard to the patient's safety.

The principal object of the invention, therefore, is to provide a substantially stress-free box lock joint having greater durability than conventional box lock joints. A second object of the invention is to insure against the loss of the hinge pin or parts thereof in the event of hinge pin breakage. Further objects of the invention include the simplification of the manufacturing process and the production of a box lock joint having as little play as possible. Still other objects will be apparent from the following detailed description when read in conjunction with the drawings.

BRIEF DESCRIPTION OF THE DRAWINGS

FIG. 1 is a perspective view of a box lock clamp in accordance with the invention;

FIG. 2 is a partially cut away side elevation of a square punched box lock joint in accordance with the prior art;

FIG. 3 is a bottom plan view of the joint of FIG. 2;

FIG. 4 is a partially cut away side elevation of a star punched box lock joint in accordance with the prior art;

FIG. 5 is a bottom plan view of the joint of FIG. 4;

FIGS. 6 through 9 are vertical sections taken through a box lock joint in accordance with the invention, illustrating the successive steps of manufacture;

DETAILED DESCRIPTION

Figure 10:
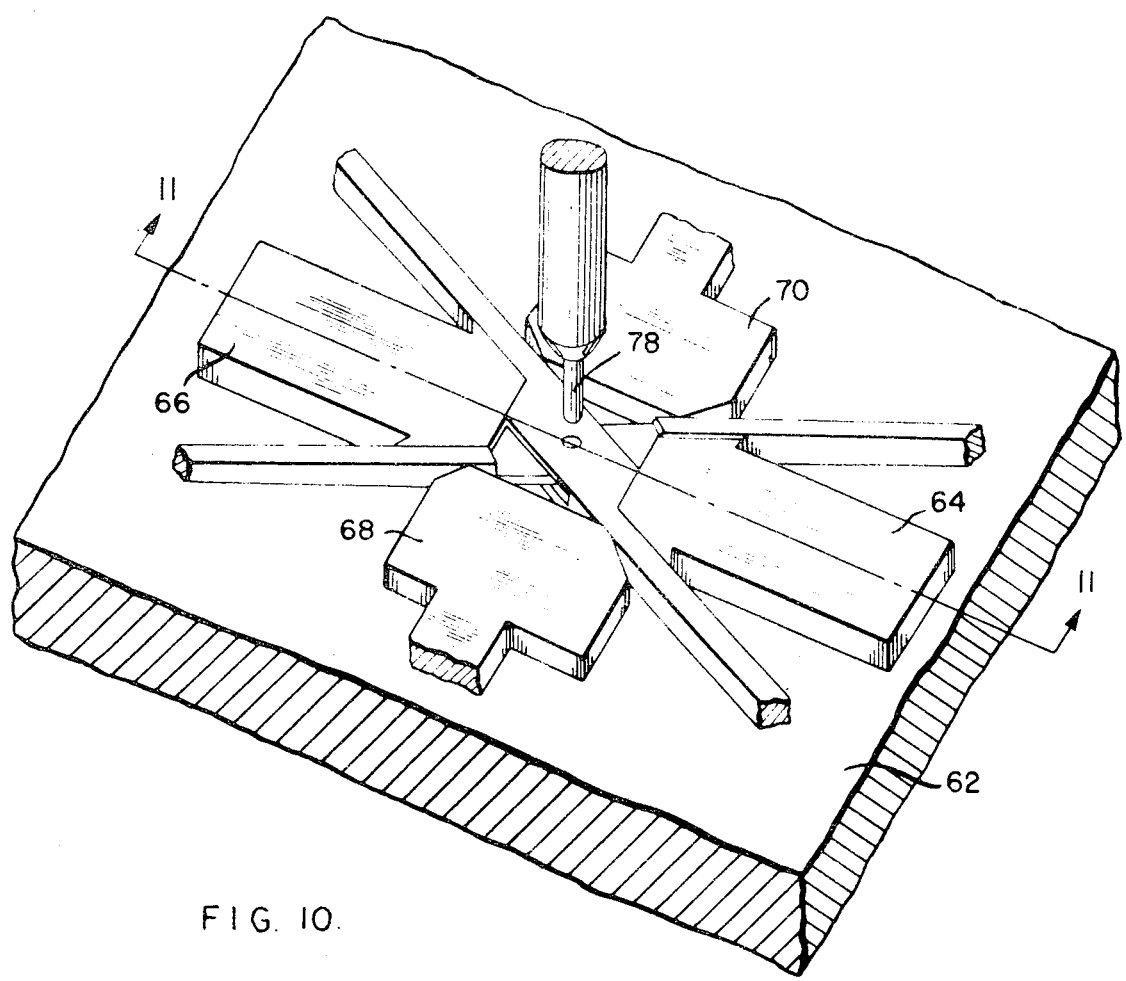
FIG. 10 is a perspective view of a fixture used in the manufacture of a box lock surgical instrument in accordance with the invention.

In FIG. 1, a box lock surgical clamp generally indicated at 12 comprises a pair of members 14 and 16 joined together by a box lock joint generally designated 18. A jaw 20 on member 14 is arranged to cooperate with jaw 22 on member 16. Movement of the jaws toward and away from each other is controlled by manipulable rings 24 and 26. Latching means adapted to set the jaws in any desired one of a number of discrete positions comprise ratchet 28 and cooperating tooth 30 respectively on members 14 and 16.

Member 14 has a bifurcated portion at the location of the joint whereby jaw 20 and ring 24 are connected by two separate elements 32 and 34 having between them a slot 36. Internally, slot 26 has substantially flat, parallel sides. A portion 38 of member 16, machined to conform with the flat inner surfaces of slot 36 extends through the slot with jaw 22 and ring 26 on opposite sides of the bifurcated portion of member 14. A hinge pin (not shown in FIG. 1) extends across the interior of the slot and through a hole in element 38. The hinge pin allows the jaws to be controlled by the manipulation of rings 24 and 26.

As described thus far, the instrument is entirely conventional. In manufacture in accordance with conventional methods, forged members corresponding to members 14 and 16 of the finished product are joined by spreading apart the elements corresponding to elements 32 and 34 of member 14, inserting member 16 between those elements, and bringing elements 32 and 34 back to their normal relationship. A hole is drilled through the elements corresponding to elements 34, 38 and 32, and a temporary pin is inserted to keep the parts in alignment during formation of the jaws and other necessary bending and machining operations. The temporary pin is then removed, and the members corresponding to members 32 and 34 are punched to a square configuration as shown in FIG. 3, or to a multiple-point or "star" configuration as shown in FIG. 5. The elements of the instrument are then hardened, and the final hinge pin is inserted and swaged into place. Following swaging, final finishing of the instrument takes place. FIGS. 2, 3, 4 and 5 illustrate two box lock joints in accordance with the prior art. In FIG. 2, it will be noted that the pin 40 is held in place only by reason of the fact that the swaging step widens its ends to fill the square configuration of the holes in the outer elements of the joint. This is also the case in FIG. 4 in which the ends of pin 42 are swaged to fill the six-pointed star configuration of the holes in the outer elements of the joint. In either case, the pin depends on its own integrity to hold it in place. Should it break by reason of a material failure transverse to the longitudinal axis, the pin could fall into the patient during an operation. As previously stated, the box lock joint, as illustrated in FIGS. 2, 3, 4 and 5 is subject to breakage by reason of the stresses produced by the swaging operation.

FIGS. 6, 7, 8 and 9 illustrate successive steps in the production of the fused box lock joint in accordance with the invention. As shown in FIG. 6, a pin 44 having a head 46 is inserted into aligned holes in the elements of the box lock joint, the inner element being designated 48, and the outer elements being designated 50 and 52. The head 46 is larger in diameter than the hole in element 50, and the pin is thus retained for the first fusing operation.

FIG. 7 illustrates the result of the first fusing operation. The head is transformed into a weld 54 which securely fastens pin 44 to element 50 of the joint. Weld 54 has a 100% depth of penetration in element 50. This is not difficult to achieve, and optimum fusion time for a given size of instrument can be easily determined. When a 100% depth is reached, there is a considerable time lag before the current tends to weld element 50 to element 48. Thus, there is considerable leeway in the range of fusion time which will produce a good weld with 100% penetration depth.

Following the first fusion step, the instrument is turned upside down, and a second fusion step takes place which fuses the protruding end of pin 44 to element 52, producing a weld 56, as shown in FIG. 8, which is similar to weld 54.

Finally, the excess fused material is ground away, and the instrument is subjected to any necessary final finishing steps and polishing. The final operations produce smooth surfaces 58 and 60, as shown in FIG. 9. The pin is invisible. Except for the fact that the pin is invisible, the instrument made in accordance with the invention resembles conventional instruments.

Figure 11:
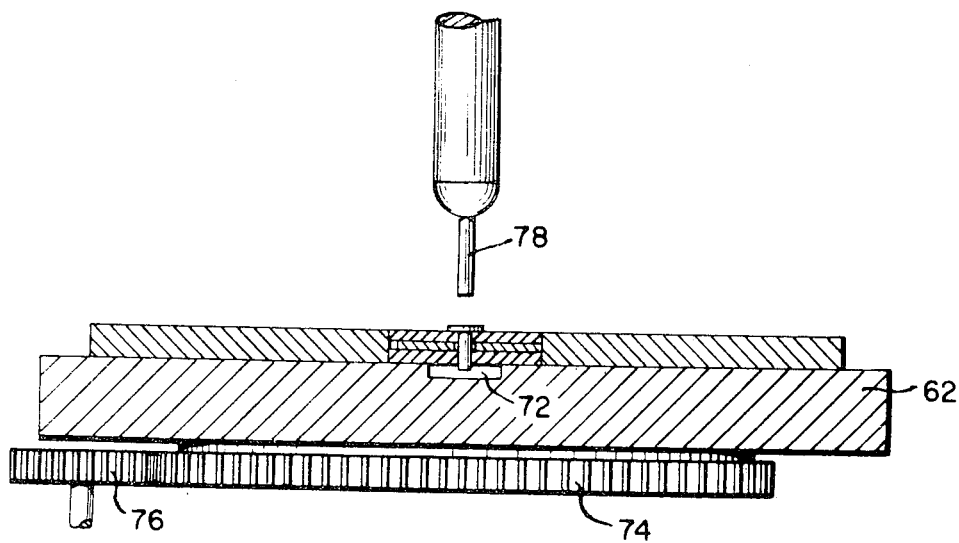
FIG. 11 is a vertical section of the fixture of FIG. 10.

Preferably, a special fixture, such as that shown in FIGS. 10 and 11, is used for the drilling and fusion operations in accordance with the invention. The fixture comprises a base 62 on which are mounted specially shaped clamps including fixed clamps 64 and 66 and slidable clamps 68 and 70. The clamps hold the elements of the instrument securely in a fixed position as shown for drilling of the aligned holes. Base 62, as shown in FIG. 11, is provided with a depression 72 for drilling and also in order to accommodate the protruding end of the pin. The base is mounted on gearing including gear 74 and pinion 76 for rotation of the base during fusion to insure a uniform weld. An electrode 78 is shown in FIGS. 10 and 11 in position just above the pin.

By way of specific example, a DeBakey ring handle bulldog clamp having an overall length of about 5 inches and consisting of 410 stainless steel is assembled in accordance with the invention using a headed 0.075 inch diameter, 0.195 inch long pin, also of 410 stainless. The instrument is drilled to 0.078 inches. Fusion takes place at 32 amperes for 12 seconds with the electrode centered above the pin and spaced 0.037 inches from the head of the pin. The base is rotated at 10 rpm so that it rotates through two complete revolutions during each fusing step. The foregoing produces a 100% weld on each side of the box lock joint without fusing the elements of the box lock joint together.

A DeBakey angled straight jaw peripheral vascular clamp having an overall length of 7 inches, a pin length of 0.230 inches and a pin diameter of 0.090 inches and otherwise similar to the above-mentioned bulldog clamp is assembled under the same conditions as listed above, except that the instrument is drilled to 0.093 inches and a current of 35 amperes is used.

A 10 inch DeBakey tangential occlusion clamp having a pin length of 0.271 inches and a pin diameter of 0.093 inches, and otherwise similar to the above-mentioned clamps is assembled under the same conditions as the above-mentioned vascular clamp except that the fusion current is set at 38 amperes.

Heavier instruments are assembled by the use of a longer fusing time, or a heavier fusing current, or both, and smaller instruments are assembled using a shorter time or a lighter fusing current. The required conditions can be easily determined for any given instrument. Furthermore, the nature of the process allows for the production of uniform 100% welds with a large margin of error in fusing conditions.

The process produces an exceptionally strong and reliable box lock joint. Since no swaging of the pin takes place, the stresses which resulted in failures of prior art instruments are not set up. Furthermore, since hardening takes place following fusion, any stresses which are present as a result of bending or machining or fusing steps are relieved in the process of hardening the instrument. In addition, since the hinge pin is secured by fusing to the outer elements of the box lock joint, it is prevented from falling out of the instrument even if it is broken in use.

We claim:

1. A box lock surgical instrument comprising first and second members each having, at one end, operative means adapted to cooperate with the operative means of the other member, and each having at its opposite end manipulable means for controlling the movement of the operative means on the said member, the first member having a bifurcated portion at an intermediate location whereby its operative means and its manipulable means are connected by two separate elements having a slot between them and the second member extending through said slot with its operative means and its manipulable means on opposite sides of said bifurcated portion, a hole extending through the portion of the second member located between said separate elements, and a pin extending through said hole and welded at its opposite ends to said separate elements, said pin being welded, at each of its opposite ends, to one of said separate elements throughout a weld zone which extends through at least 75% of the thickness of said one of said separate elements.

2. A box lock surgical instrument according to claim 1 wherein the demarcation between said pin and the outer surfaces of said separate elements is invisible.

3. A box lock surgical instrument according to claim 1 wherein the box lock is substantially stress-free.

4. A box lock surgical instrument according to claim 1 wherein, at each of its opposite ends, said pin is welded to one of said separate elements throughout a weld zone which extends through substantially 100% of the thickness of said one of said separate elements.

* * * * *